United States Patent [19]

Nash

[11] Patent Number: 4,527,977
[45] Date of Patent: Jul. 9, 1985

[54] GAS-DRIVEN DENTAL SCALER HAVING TORQUE REACTION MEANS

[75] Inventor: John E. Nash, Downingtown, Pa.

[73] Assignee: Syntex (U.S.A.) Inc., Palo Alto, Calif.

[21] Appl. No.: 234,283

[22] Filed: Feb. 13, 1981

Related U.S. Application Data

[63] Continuation-in-part of Ser. No. 12,631, Feb. 16, 1979, abandoned.

[51] Int. Cl.³ .............................................. A61C 1/07
[52] U.S. Cl. .................................................. 433/120
[58] Field of Search ............... 433/119, 118, 117, 120, 433/143

[56] References Cited

U.S. PATENT DOCUMENTS

Re. 29,687  7/1978  Sertich ............................. 433/120
4,260,380  4/1981  Nash ................................. 433/120

Primary Examiner—Robert Peshock
Attorney, Agent, or Firm—John A. Dhuey

[57] ABSTRACT

A gas-driven dental scaling instrument having a resiliently mounted vibratable tube-and-rotor vibrating mechanism is disclosed, which instrument includes torque reaction means to oppose twisting forces applied to the vibratable tube supported on its resilient mountings during engagement or disengagement of a work tool with or from one end of the vibratable tube.

15 Claims, 6 Drawing Figures

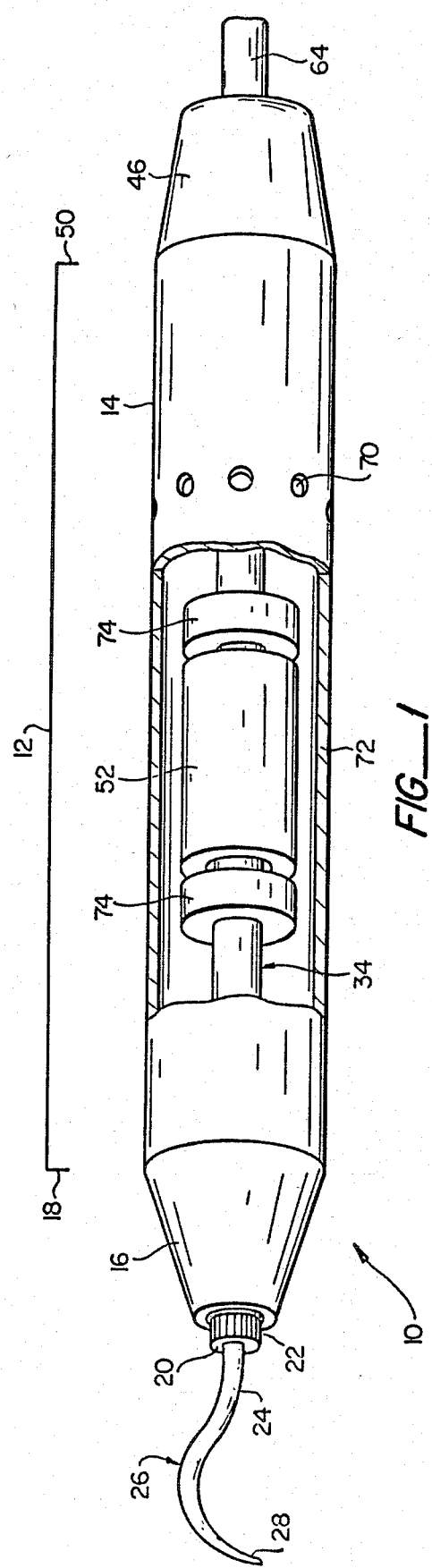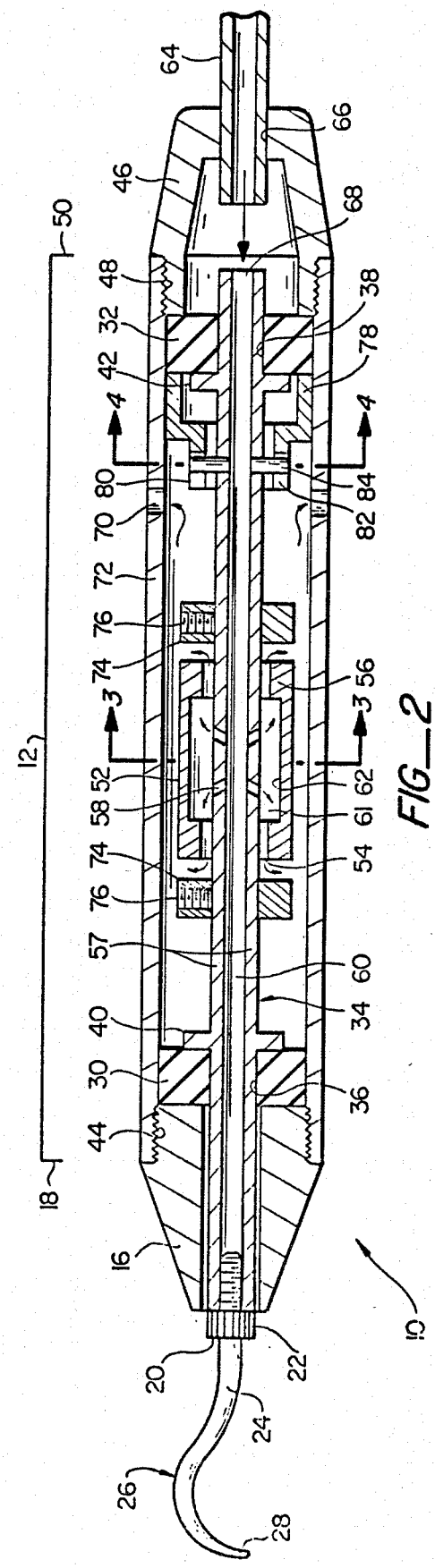

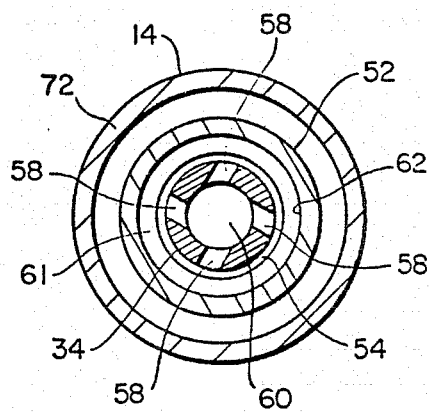
FIG_3
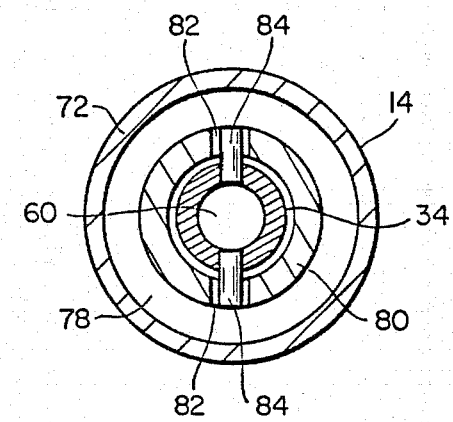
FIG_4
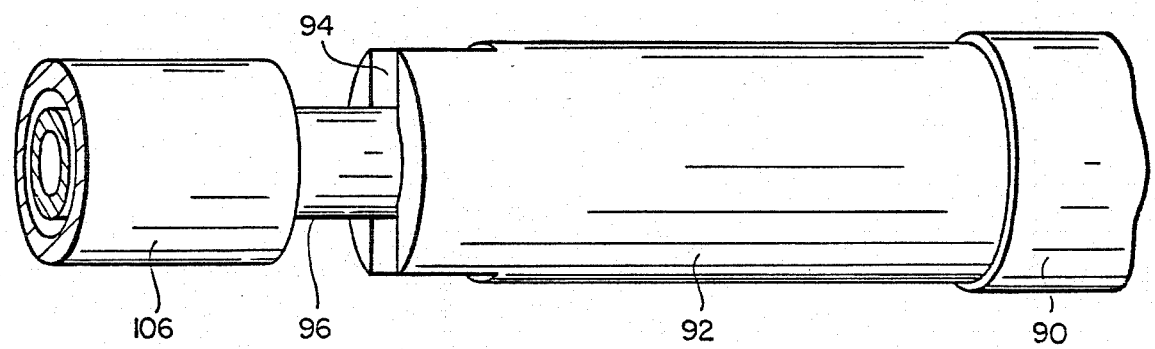
FIG_5
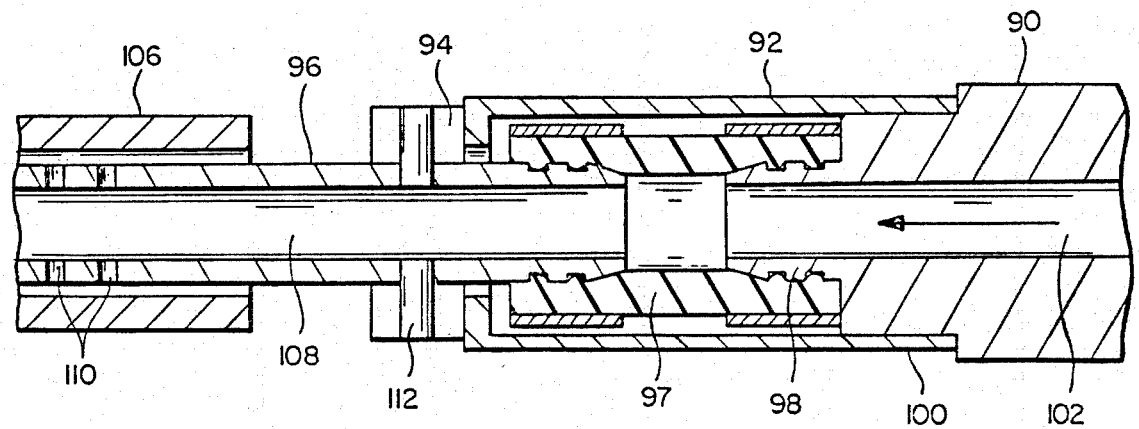
FIG_6

GAS-DRIVEN DENTAL SCALER HAVING TORQUE REACTION MEANS

RELATED APPLICATIONS

This application is a continuation-in-part of copending application Ser. No. 12,631, filed Feb. 16, 1979 and now abandoned, the entire disclosure of which is incorporated herein by reference.

BACKGROUND OF THE INVENTION

1. Field

Power driven dental scalers are well known. Of particular interest herein is a dental scaler which utilizes compressed air to drive a vibrating element within the scaler.

2. State of the Art

Of the power driven dental scalers currently available, most common are scalers utilizing a flow of compressed air or an electrical ultrasonic transducer to cause a scraping type work tool to vibrate.

Typical of the earlier air-driven dental scalers are those of U.S. Pat. Nos. 3,082,529 and 3,444,622 to Mills et al, which scalers utilize an air-driven ball contained in a chamber. Movement of the ball against the walls of the chamber imparts vibration to the chamber which vibrations are then transmitted to the scraping tool. A more recent type of air-driven scaler, described in U.S. Pat. No. 3,526,962 to Fuerst, utilizes a rotatable mandrel which has an irregularly-shaped tip engaged with a reciprocable block in which the mandrel tip is received.

It is characteristically a problem of these air driven scalers that much of the vibrational energy generated by the vibrator motor is transferred to the handle portion of the dental scaler rather than to the scraper work tool. Moreover, the modes of vibration of these scalers may change as moving parts of the vibration generating mechanism wear with time.

In U.S. Pat. No. 3,703,037 to Robinson, there is described a dental scaler which utilizes an electrical ultrasonic transducer to provide constant modes of vibration for coupling with particular types of work tools. One disadvantage of the ultrasonic scaler, however, is the cost of the transducer and its fairly sophisticated ultrasonic generator.

A recent improvement in air-driven dental scalers is disclosed in U.S. Pat. Re. No. 29,687 to Sertich. This dental scaler has very few moving parts as compared to the aforementioned mechanically complicated air-driven scalers and provides efficient transfer of vibrational energy to a scraping-type work tool with generation of relatively little noise and minimal vibration being transferred to the handle portion of the instrument. Moreover, the Sertich-type scaler provides uniform modes of constant vibration which may be matched with the vibratory modes of various types of work tools without the need for complicated electronic components.

The Sertich-type dental scaler achieves these advantages in part by including a single, rigid vibratable tube mounted on resilient support washers disposed at or near the theoretical vibratory nodes characteristic of the natural vibrational mode of the tube. A work tool, such as a scraper or a pick, is typically secured to the working end of the vibratable tube by a connection between an externally-threaded work tool shank and an internally threaded portion of the tube. Often times it may be difficult to securely attach the work tool to the vibratable tube inasmuch as torque applied to tighten the work tool may result in twisting of the tube within its resilient supports, thus preventing proper and safe attachment of the work tool to the dental instrument. Moreover, even if proper securement of the work tool to the scaler is attained, then excessive torque applied to remove the work tool may result in dislocation or distortion of the resilient supports.

There is, therefore, need for an air-driven dental scaler of the Sertich-type in which proper tightening and loosening of a threaded work tool shank from a resiliently supported vibratable member may be achieved without adversely affecting the resilient supports.

SUMMARY OF THE INVENTION

An air-driven, vibratory-type dental scaler having a resiliently supported vibratable element to which a work tool can be safely and securely attached and easily detached therefrom is provided by an elongated casing means having a proximal end and a distal end, resilient support means within the casing means, a rigid shaft supported within the casing means by the resilient support means, work tool connecting means attached to the distal end of the rigid shaft, the work tool connecting means capable of operatively connecting a work tool to the distal end of the rigid shaft, means for imparting vibration to the resiliently supported rigid shaft to provide vibratory movement to a work tool connected to the work tool connecting means, and torque reaction means affixed to the casing means and associated with the rigid shaft for resisting torque applied to the rigid shaft during tensional engagement or disengagement of a work tool with the work tool connecting means.

The torque reaction means provides resistance to twisting moments applied to the rigid shaft when a threaded work tool shank is tightened onto, or loosened from, a threaded portion of the shaft. The torque reaction means can comprise a substantially cylindrical torque reaction tube coaxially disposed about one end of the rigid shaft, there being lost motion connecting means connecting the substantially cylindrical tube with the rigid shaft. In one embodiment, the lost motion connecting means may comprise a slot in one end portion of the substantially cylindrical torque reaction tube.

A pin affixed to the shaft and protruding outwardly of the shaft in a direction transverse to the axis of the shaft extends into the slot. The pin is preferably smaller than the slot so that a gap exists between the slot and the pin. Such an arrangement may be termed a "lost motion" connection inasmuch as some twisting movement of the shaft is provided before the pin engages the slot. Since the torque reaction tube is affixed to the casing means of the dental scaler, engagement of the shaft pin with the torque tube slot resists or prevents further rotation of the shaft, such as may occur when a threaded work tool shank is tightened onto a threaded portion of the shaft.

The gap provided between the pin and slot precludes transfer of vibration from the vibratable shaft to the handle portion of the shaft. Thus the lost motion connection between the shaft and the torque reaction tube provides means for resisting clockwise and counterclockwise twisting forces applied to the shaft while at the same time the vibration-damping character of the resilient suspension is preserved.

In another aspect of the invention, the torque reaction means comprises means for returning the rigid shaft to an operative position wherein the transfer of vibration from the rigid shaft to the casing means is substantially prevented. The lost motion connecting means limits rotation of the rigid shaft at a first position and a second position during torsional engagement or disengagement, respectively, of a work tool with the work tool connecting means. The return means returns the rigid shaft to an operative position between the first position and the second position after torsional engagement or disengagement of a work tool with the work tool connecting means, such that the lost motion connecting means substantially prevents the transfer of vibration from the rigid shaft to the casing means when the shaft is in its operative position during operation of the instrument.

The means for imparting vibration to the resiliently supported rigid shaft may comprise the mechanism disclosed in the aforementioned U.S. Pat. Re. No. 29,687, the disclosure of which is incorporated herein by reference. The rigid shaft thus can comprise a tube supported at spaced apart portions of the tube by resilient support means. Rotor means operatively associated with the tube and disposed axially parallel to the axis of the tube is drivable in a generally circular direction with respect to the tube by fluid media. Each of the tube and rotor means has a configuration and is disposed with respect to the other so as to define a space for receiving the fluid media during movement of the rotor means with respect to the tube. The tube includes fluid media inlet means and outlet means, respectively, for receiving and discharging fluid media into the defined space between the tube and the rotor means. Fluid media, such as compressed air, flows through the inlet means into the defined space and drives the rotor means about the tube. Contact of the rotor means with the tube during rotation imparts vibratory movement to the tube.

The vibratory driving mechanism of the invention, which includes a portion of the tube, the rotor means and the fluid media inlet and outlet means, could be any of several configurations. In one embodiment, the fluid media inlet means may comprise an opening in one end of the tube adjacent the proximal end of the casing. The fluid media outlet means can comprise one or more ports in the sidewall of the vibratable tube, each of the ports having an axis spaced from, or offset from, the longitudinal axis of the tube. The rotor means may be a sleeve having an inner diameter slightly greater than the outer diameter of the tube. The sleeve will be disposed with respect to the tube so that one or more of the tube outlet ports may discharge fluid media into the defined space between the sleeve and the tube.

DESCRIPTION OF PREFERRED EMBODIMENTS

The means providing the features and advantages of the present invention are illustrated in the accompanying drawings wherein:

FIG. 1 is a perspective view, partly in section, of a dental scaling instrument;

FIG. 2 is a longitudinal cross sectional view of the dental scaler of FIG. 1;

FIG. 3 is a cross-sectional view of the vibratory driving mechanism of the dental scaler of FIG. 2 taken along line 3—3;

FIG. 4 is a cross-sectional view of the torque reaction means of the invention taken along line 4—4 of FIG. 2;

FIG. 5 is a perspective view of another embodiment the torque reaction means of the invention associated with a vibratory driving mechanism similar to that of FIG. 3; and FIG. 6 is a longitudinal cross-sectional view of the torque reaction means of FIG. 5.

Illustrated in FIG. 1 is a dental scaling instrument 10 comprising a handle 12 which includes a barrel 14 and a neck 16. Attached to the distal end 18 of handle 12 is a nose piece 20 having an outer knurled wall 22. Secured within nose piece 20 is a shank 24 of a work tool 26 having a configuration of a curved scaler tip 28. As shown in detail in the cross-sectional view of FIG. 2, handle 12 provides an elongated casing within which are mounted resilient support means comprising a first or front resilient support bushing 30 and a second or rear resilient support bushing 32. Disposed substantially coaxially with respect to elongated handle 12 is a vibratable shaft in the form of a tube 34 which passes through axially disposed openings 36 and 38, respectively, in bushings 30 and 32, and in its operative condition provides an orbit of motion to work tool 26. Substantial axial movement of tube 34 is prevented by first and second flanges 40 and 42 which rest against bushings 30 and 32, respectively. First support bushing 30 is retained within the elongated casing by neck 16 which is threadedly engaged with inner wall portion 44 at distal end 18 of handle 12. Similarly, cap 46, which is threadedly engaged with inner wall portion 48 at proximal end 50, retains second support bushing 32 within the elongated casing provided by handle 12.

Disposed about a mid-portion of tube 34 is a sleeve-like rotor 52. As shown in FIG. 2, rotor 52 is disposed substantially coaxially with respect to tube 34, there being annular gaps 54 established between annular-shaped end portions 56 of rotor 52 and adjacent portions of side wall 57 of tube 34. In an actual assembly with rotor 52 at rest, rotor 52 will be supported upon tube 34 so that a portion of each of the annular ends 56 will rest upon side wall portions of tube 34. Located in side wall portions of tube 34 is a plurality of outlet ports 58 which connect passageway 60 of tube 34 to a chamber 61 defined by inner wall 62 of rotor 52 and an adjacent portion of tube side wall 57.

As indicated by the arrows in FIG. 2, a fluid medium, such as compressed air, is supplied from a source (not shown) through a supply tube 64 which passes through an axially disposed opening 66 in cap 46. The flow of compressed air passes into fluid media inlet port 68 and through passageway 60 to fluid media outlet ports 58. The flow of compressed air which exhausts through outlet ports 58 fills chamber 61. The force of impact of the air on inner wall 62 of rotor 52 urges rotor 52 into an orbit of revolution about the longitudinal axis of tube 34. As shown in FIG. 3, each of outlet ports 58 has an axis which is offset or spaced at a distance from the longitudinal axis of tube 34, such that each port axis does not intersect the axis of tube 34. Thus each of ports 58 directs a jet of air at a glancing angle with respect to the inner wall 62 of rotor 52 so as to impart rotary movement to rotor 52. Also, as shown in FIG. 2, outlet ports 58 are preferably angled with respect to a plane which is perpendicular to tube 34 and which bisects rotor 52, so that air discharged from half of the plurality of ports 58 impart a component of force tending to move rotor 52 in the distal direction, while air discharged from the other half of the plurality of ports 58 impart a component of force tending to move rotor 52 in the proximal direction.

After imparting rotary movement to rotor 52, the air exhausts from chamber 61 through fluid media outlet ports as provided by annular gaps 54 defined by annular end portions 56 and tube side wall 57. The air is further exhausted from the interior of barrel 14 through exhaust ports 70 disposed circumferentially about a rearward portion 72 of barrel 14. Stop means comprising annular-shaped guides 74 are affixed to tube 34 by set screws 76. Guides 74 are positioned adjacent either end of rotor 52 so as to limit movement of rotor 52 in the axial direction along tube 34.

The speed of revolution of rotor 52 about tube 34 is generally dependent upon the size, number and angles of incidence of the air streams discharged from outlet ports 58, and the velocity thereof. A description of the manner in which the spinning rotor 52 imparts vibration to tube 34 may be found in the aforementioned U.S. Pat. Re. No. 29,687.

The illustrated dental scaler further includes torque reaction means to resist twisting movement applied to tube 34 when work tool 26 is tightened onto or loosened from tube 34. As shown in FIG. 2, the torque reaction means includes a sleeve 78 fixedly engaged with the inner surface of barrel wall portion 72. Sleeve 78 has an extended portion 80 which includes a pair of longitudinal slots 82 disposed on opposite sides of sleeve extended portion 80. Affixed to tube 34 in alignment with each of the opposed slots 82 is a pin 84, which pins 84 extend transversely of the axis of tube 34 in radially outward directions from tube 34. Pins 84 fit loosely and are centered within slots 82 so that there is no metal to metal contact between each pin 84 and sleeve extended portion 80. One, or both, of pins 84 thus provide stop means which coact with sleeve extended portion 80 to limit rotational movement of tube 34 with respect to sleeve 78 at a first position and a second position during torsional engagement or disengagement, respectively, of the work tool. The gap which exists between pin 84 and sleeve extended portion 80 within slot 82 provides a "lost motion connection", that is, tube 34 may be twisted a short distance in the clockwise or counter-clockwise direction before contact is made between pin 84 and sleeve extended portion 80. Thus when tube 34 is vibrating during use of the instrument, vibrations are not normally transmitted between pin 84 and sleeve 78. The torque reaction means limits movement of tube 34 within its resilient mountings by resisting the twisting force applied to tube, after the lost motion is taken up when a work tool is tightened onto or loosened from tube 34.

Depicted in FIGS. 4 and 5 is another embodiment of the torque reaction means of the invention. The torque reaction means comprises a sleeve 90 adapted to be fixedly engageable with the inner wall of a handpiece housing or instrument barrel. A sleeve extension 92 has a diameter substantially less than that of sleeve 90. A portion of sleeve extension 92 provides a slot 94.

Vibratable tube 96 is mounted within sleeve extension 92 upon a resilient support as provided by a cylindrical tube or cylinder 97 of resilient material. One end of cylinder 97 is engaged around a boss 98 which is integrally formed with the body portion 100 of the torque reaction means. The other end of cylinder 97 is engaged about a proximal end portion of vibratable tube 96. A passageway 102 provides means for transmitting air through the torque reaction means to the proximal end of tube 96. A rotor is provided by a sleeve 106 which has a diameter slightly larger than the outer diameter of vibratable tube 96. A fluid medium, such as compressed air, is delivered by a remote source (not shown) through passageway 102 and travels through passageway 108 within tube 96 and is then discharged through fluid media outlet ports 110. Inasmuch as each of outlet ports 110 has its axis offset from a radius extending from the center of tube 96, the compressed air discharged from outlet port 110 causes rotor sleeve 106 to revolve around tube 96 thereby imparting vibration to tube 96 as discussed with respect to the embodiment of FIGS. 1-3.

Affixed to a portion of tube 96 is a torque reaction pin 112, which projects into slot 94 of sleeve extension 92. Gaps between pin 112 and the walls defining slot 94 allow limited movement of tube 96 in the clockwise or counter-clockwise directions during tightening or loosening of a work tool threadably engaged with the distal end of vibratable tube 96. Typically, tube 96 may move as much 30° before pin 112 contacts sleeve extension 92, although more or less movement may be provided by widening or narrowing slot 94. The lost motion connection between pin 112 and slot 94 thus provides for isolation of the vibratable tube from metallic portions of sleeve extension 92 so that transmission of vibration from tube 96 to the handle portion is minimized.

Resilient support 97 functions as a return means for returning vibratable tube 96 to an operative position at which pin 112 is spaced from the walls defining slot 94. Vibratable tube 96 thus is isolated in its operative position from the casing of the instrument and the transfer of vibration from vibratable tube 96 to the metallic portions of sleeve extension 92 and subsequently to the housing or instrument casing is substantially prevented.

When a work tool is being threadedly engaged with the distal end of vibratable tube 96, resilient support 97 twists about its longitudinal axis, since it is attached to boss 98 at its one end and to the proximal end of tube 96 at its other end, and torque reaction pin 112 contacts the walls defining slot 94 at a first position to resist the twisting forces applied to vibratable tube 96.

When the work tool has been completely engaged, resilient support 97, because of its resilient nature, assumes its original, unstressed configuration and returns torque reaction pin 112 to a position spaced from the walls defining slot 94. Vibratable tube 96 accordingly is returned to an operative position whereat the transfer of vibration from vibratable tube 96 to the housing or casing of the instrument is substantially prevented during operation of the instrument.

In a similar manner, when the work tool is being disengaged from the distal end of vibratable tube 96, resilient support 97 twists in the opposite direction about its longitudinal axis and torque reaction pin 112 contacts the walls defining slot 94 at a second position to resist the twisting forces applied to vibratable tube 96. When the work tool has been completely disengaged, resilient support 97 assumes its original unstressed configuration and returns torque reaction pin 112 to a position spaced from the walls defining slot 94.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. A dental scaler comprising:
   elongated casing means having a proximal end and a distal end;
   resilient support means within said casing means;
   a substantially rigid shaft supported within said elongated casing means by said resilient support means;
   work tool connecting means attached to the distal end of said shaft, said work tool connecting means capable of operatively connecting a work tool to the distal end of said shaft;
   means for imparting vibration to said resiliently supported shaft when said dental scaler is energized to provide vibratory movement to a work tool connected to said work tool connecting means; and
   torque reaction means affixed to said elongated casing means and associated with said shaft for resisting torque applied to said shaft during torsional engagement or disengagement of a work tool with said work tool connecting means,
   said torque reaction means including lost motion connecting means for limiting rotation of said shaft at a first position and a second position during torsional engagement or disengagement, respectively, of a work tool with said work tool connecting means, said torque reaction means further including means for returning said shaft to an operative position between said first position and said second position after torsional engagement or disengagement of a work tool with said work tool connecting means, said lost motion connecting means substantially preventing transfer of vibration from said shaft to said casing means when said shaft is in said operative position during operation of the scaler.

2. The dental scaler of claim 1 wherein said torque reaction means comprises
   a substantially cylindrical torque reaction tube coaxially disposed about one end of said shaft.

3. The dental scaler of claim 2 wherein said lost motion connecting means comprises a slot in one end portion of said substantially cylindrical torque reaction tube and a pin affixed to said shaft transversely with respect to said shaft, said pin engaging said slot so as to form a lost motion connection between said torque reaction tube and said shaft to limit rotation of said shaft within said tube.

4. The dental scaler of claim 1 wherein said returning means comprises resilient means attached to said shaft and to said casing means.

5. The dental scaler of claim 4 wherein said resilient means attached to said shaft comprises a cylindrically-shaped tube.

6. The dental scaler of claim 1 wherein said returning means comprises a cylindrically-shaped tube of resilient material, one end of which is in overlying and frictional engagement with the proximal end of said shaft, and
   a rigid support member capable of frictional engagement with the casing means of the dental scaler, said rigid support member having a boss portion frictionally engaged with the other end of said cylindrically-shaped tube.

7. The dental scaler of claim 6 wherein said lost motion connecting means comprises a sleeve fixedly attached to said rigid support member with said sleeve overlying said cylindrically-shaped tube of resilient material, said sleeve having at least one slot therein overlying a portion of the proximal end of said shaft, and stop means fixedly attached to a portion of said shaft at its proximal end, said stop means comprising at least one pin extending transversely of the axis of said shaft and into said slot, said slot and said pin having dimensions creating a gap between said pin and each of the walls of said slot so as to form a lost motion connection between said sleeve and said shaft.

8. The dental scaler of claim 1 wherein said said shaft comprises a tube having a side wall, said tube supported along spaced apart portions of said side wall by said resilient support means, said tube including fluid media inlet means and outlet means, respectively for receiving and discharging a fluid media;
   said means for imparting vibration comprises rotor means operatively associated with said tube and disposed axially parallel with respect to the axis of said tube, said rotor means drivable in a generally circular direction with respect to said tube by the fluid media;
   said tube and said rotor means each having a configuration and disposed with respect to each other so as to define a space therebetween for receiving the fluid media during movement of said rotor means with respect to said tube;
   whereby fluid media flowing through said inlet means into the space drives said rotor means rotatably with respect to said tube so that said rotor means imparts vibratory movement to said tube.

9. The dental scaler of claim 8 wherein
   said fluid media inlet means comprises an opening in one end of said tube adjacent the proximal end of said casing;
   said fluid media outlet means comprises one or more ports in the sidewall of said tube, each of said ports having an axis spaced from the longitudinal axis of said tube;
   said rotor means is a sleeve having an inner diameter slightly greater than the outer diameter of said tube, and said sleeve is disposed with respect to said tube so that one or more of said tube outlet ports discharge fluid media into the space between said sleeve and said tube.

10. In a dental scaler having a vibration-generating system mountable within housing means, the vibration-generating system comprising a vibratable shaft having a proximal end and a distal end, the shaft in its operative condition providing an orbit of motion to a work tool detachably mountable upon the distal end of the shaft, the vibration-generating system including first and second resilient support means for resiliently supporting the vibratable shaft within the housing means, the improvement comprising:
   torque reaction means associated with said vibratable shaft for resisting torque applied to said shaft during torsional mounting or demounting of a work tool to or from the distal end of the shaft,
   said torque reaction means including lost motion connecting means for limiting rotation of said shaft at a first position and a second position during torsional engagement or disengagement, respectively, of the work tool with the distal end of the shaft, said torque reaction means further including means for returning said shaft to an operative position between said first position and said second position after torsional engagement or disengagement of a work tool with said work tool connecting means, said lost motion connecting means substantially preventing transfer of vibration from said shaft to said housing means which said shaft is in said operative position during operation of the scaler.

11. The improvement of claim 10 wherein said torque reaction means comprises a substantially cylindrical torque reaction tube coaxially disposed about one end of said shaft, and said lost motion connecting means comprising a slot in one end portion of said substantially cylindrical tube and a pin affixed to said shaft transversely with respect to said shaft, said pin and said slot having dimension creating a gap between said pin and the walls of said slot so as to form a lost motion connection in every direction between said tube and said shaft to prevent the transfer of vibration and limit rotation of said shaft within said tube.

12. A dental scaler comprising:
elongated casing means having a proximal end and a distal end;
resilient support means within said casing means;
a substantially rigid shaft supported within said elongated casing means by said resilient support means;
work tool connecting means attached to the distal end of said shaft, said work tool connecting means capable of operatively connecting a work tool to the distal end of said shaft;
means for imparting vibration to said resiliently supported shaft when said dental scaler is energized to provide vibratory movement to a work tool connected to said work tool connecting means; and
torque reaction means affixed to said elongated casing means and associated with said shaft for resisting torque applied to said shaft during torsional engagement or disengagement of a work tool with said work tool connecting means,
said torque reaction means including lost motion connecting means for limiting clockwise or counter-clockwise rotation of said shaft during torsional engagement or disengagement of a work tool with said work tool connecting means, said torque reaction means comprising a substantially cylindrical torque reaction tube coaxially disposed about one end of said shaft, and said lost motion connecting means comprising a slot in one end portion of said substantially cylindrical tube and a pin affixed to said shaft transversely with respect to said shaft, said pin and said slot having dimensions creating a gap between said pin and the walls of said slot so as to form a lost motion connection in every direction between said tube and said shaft to prevent the transfer of vibration and limit rotation of said shaft within said tube.

13. In a dental scaler having a vibration-generating system mountable within housing means, the vibration-generating system comprising a vibratable shaft having a proximal end and a distal end, the shaft in its operative condition providing an orbit of motion to a work tool detachably mountable upon the distal end of the shaft, the vibration-generating system including first and second resilient support means for resiliently supporting the vibratable shaft within the housing means, the improvement comprising:
torque reaction means associated with said vibratable shaft for resisting torque applied to said shaft during torsional mounting or demounting of a work tool to or from the distal end of the shaft,
a first resilient support connected to the proximal end of said vibratable shaft, said first resilient support comprising a cylindrically shaped tube one end of which is in overlying and frictional engagement with said vibratable shaft, and
a rigid support member capable of frictional engagement with the housing means of the dental scaler, said rigid support member having a boss portion frictionally engaged with the other end of said cylindrically shaped tube of said first resilient support.

14. The improvement of claim 13 wherein said torque reaction means comprises
a sleeve fixedly attached to said rigid support member with said sleeve overlying said first resilient support, said sleeve having at least one slot therein overlying a portion of the proximal end of said vibratable shaft; and
stop means fixedly attached to a portion of said vibratable shaft at its proximal end, said stop means comprising at least one pin extending transversely of the axis of said shaft and into said slot, said slot and said pin having dimensions sufficient to provide a lost motion connection between said vibratable shaft and said sleeve in a direction clockwise or counter-clockwise of the axis of said vibratable shaft.

15. In a dental scaler having a vibration-generating system mountable within housing means, the vibration-generating system comprising a vibratable shaft having a proximal end and a distal end, the shaft in its operative condition providing an orbit of motion to a work tool detachably mountable upon the distal end of the shaft, the vibration-generating system including first and second resilient support means for resiliently supporting the vibratable shaft within the housing means, the improvement comprising:
torque reaction means associated with said vibratable shaft for resisting torque applied to said shaft during torsional mounting or demounting of a work tool to or from the distal end of the shaft,
said torque reaction means including lost motion connecting means limiting clockwise or counter-clockwise rotation of said shaft during torsional engagement or disengagement of the work tool with the distal end of the shaft, said torque reaction means comprising a substantially cylindrical torque reaction tube coaxially disposed about one end of said shaft, and said lost motion connecting means comprising a slot in one end portion of said substantially cylindrical tube and a pin affixed to said shaft transversely with respect to said shaft, said pin and said slot having dimensions creating a gap between said pin and the walls of said slot so as to form a lost motion connection in every direction between said tube and said shaft to prevent the transfer of vibration and limit rotation of said shaft within said tube.

* * * * *